United States Patent [19]

Bansemir et al.

[11] Patent Number: 5,030,659

[45] Date of Patent: Jul. 9, 1991

[54] DISINFECTANT COMPOSITIONS

[75] Inventors: Klaus Bansemir, Langenfeld; Karlheinz Disch, Haan; Klaus Hachmann, Hilden, all of Fed. Rep. of Germany

[73] Assignee: Henkel Kommanditgesellschaft auf Aktien, Duesseldorf-Holthausen, Fed. Rep. of Germany

[21] Appl. No.: 477,159

[22] Filed: Feb. 8, 1990

Related U.S. Application Data

[63] Continuation of Ser. No. 344,411, Apr. 25, 1989, abandoned, which is a continuation of Ser. No. 936,417, Dec. 1, 1986, abandoned.

[30] Foreign Application Priority Data

Dec. 2, 1985 [DE] Fed. Rep. of Germany ....... 3542516

[51] Int. Cl.$^5$ .................... A01N 31/08; A01N 33/12; A01N 37/52
[52] U.S. Cl. .................... 514/635; 514/631; 514/642; 514/643; 514/731; 514/736; 514/737
[58] Field of Search ............... 514/635, 642, 643, 731, 514/736, 737

[56] References Cited

U.S. PATENT DOCUMENTS

| | | | |
|---|---|---|---|
| 2,684,924 | 7/1954 | Rose et al. | 167/30 |
| 2,990,425 | 6/1961 | Senior | 260/501 |
| 3,468,898 | 9/1969 | Cutler et al. | 260/301 |
| 4,022,834 | 5/1977 | Gundersen | 260/564 B |
| 4,053,636 | 10/1977 | Eustis, III et al. | 424/326 |
| 4,125,628 | 11/1978 | Goldhaft et al. | 424/329 |
| 4,198,392 | 4/1980 | Juneja | 424/48 |
| 4,321,257 | 3/1982 | Sipos | 424/809 |
| 4,420,484 | 12/1983 | Gorman et al. | 424/326 |

FOREIGN PATENT DOCUMENTS

| | | | |
|---|---|---|---|
| 99209 | 1/1984 | European Pat. Off. | |
| 0141628 | 5/1985 | European Pat. Off. | 514/635 |
| 2310989 | 2/1974 | Fed. Rep. of Germany . | |
| 3443232 | 6/1985 | Fed. Rep. of Germany . | |
| 702268 | 1/1954 | United Kingdom . | |
| 1152243 | 5/1969 | United Kingdom . | |
| 1344042 | 3/1972 | United Kingdom . | |
| 1434040 | 4/1974 | United Kingdom . | |

OTHER PUBLICATIONS

"Guidelines for Testing & Evaluating Chemical Disinfection Processes", first part, of the Deutsche Gesellschaft fur Hygiene and Mikrobiologie, Zbl. Bakt. Hyg. 1. Abt. Orig. B 172, 534–562.

*Primary Examiner*—Allen J. Robinson
*Attorney, Agent, or Firm*—Ernest G. Szoke; Wayne C. Jaeschke; Henry E. Millson, Jr.

[57] ABSTRACT

Liquid, aqueous disinfectant preparations containing a combination of
(a) at least one microbicidal quaternary ammonium compound
(b) at least one microbicidal biguanide compound and
(c) at least one microbicidal phenolic compound, components (a) and (b) being present in a ratio by weight a:b of (16 - 2); 1 while components (a) and (c) are present in a ratio by weight a:c of (16 - 2):1.

2 Claims, No Drawings

DISINFECTANT COMPOSITIONS

This application is a continuation of application Ser. No. 07/344,411, filed 04/25/89, abandoned; which is a continuation of Ser. No. 06/936,417, filed 12/01/86 abandoned.

BACKGROUND OF THE INVENTION

1. Field of the Invention

This invention relates to improved disinfectant preparations containing microbicidally active quaternary ammonium compounds and biguanide compounds.

2. Statement of Related Art

There are already a number of commercially available disinfectants which contain an activecomponent combination of microbicidal quaternary ammonium compounds and microbicidal biguanide compounds of the chlorhexidine type and of the oligomeric hexamethylene biguanide type. However, it has been found that there are gaps in the antimicrobial spectrum of these known disinfectants with respect to certain gramnegative bacteria and fungi. In addition, disinfectant preparations of the above type are susceptible to bacterial growths in storage and during periods of standing at the locus of use.

The problem which the present invention seeks to solve is to find improved disinfectants based on quaternary ammonium compounds and biguanide compounds which are not attended by any of the disadvantages mentioned above. This problem is solved by the disinfectant preparation described hereinafter.

DESCRIPTION OF THE INVENTION

The present invention relates to a liquid, aqueous disinfectant preparation containing microbicidal quaternary ammonium compounds and microbicidal biguanide compounds and which contains a combination of (a) at least one microbicidal quaternary ammonium compound,
(b) at least one microbicidal biguanide compound, and
(c) at least one microbicidal phenolic compound, and wherein components a) and b) are present in a ratio by weight of a:b of (16-2):1, and components (a) and (c) are present in a ratio by weight of a:c of (16-2):1.

Other than in the operating examples, or where otherwise indicated, all numbers expressing quantities of ingredients or reaction conditions used herein are to be understood as modified in all instances by the term "about."

Particularly suitable microbicidal quaternary ammonium,compounds (component (a) above) are compounds of the benzalkone type corresponding to the following formula $$[C_6H_5—CH_2—N(CH_3)_2R]X \quad (I)$$

in which R is a preferably straight-chain $C_8$-$C_{18}$ alkyl group and X is a halide anion, e.g. chloride, bromide, iodide; preferably chloride. These quarternary ammonium compounds can be used individually or in mixtures. Examples of antimicrobial quaternary ammonium compounds such as these are dimethylbenzyldodecylammonium chloride, dimethylbenzyltetradecylammonium chloride, dimethylbenzyl decylammonium bromide, dimethylbenzyloctylammonium chloride and cocosalkyldimethylbenzylammonium chloride, in which the cocosalkyl residue is obtained from the hydrogenated fatty acid mixture of coconut oil. Among these compounds, those in which the alkyl group R contains 12 or 14 carbon atoms are preferred.

Particularly suitable microbicidal biguanide compounds (component (b) above) are oligohexamethylene biguanide salts having a chain corresponding to the following formula

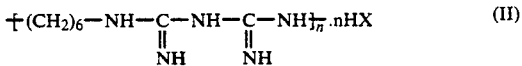

in which HX is a salt-forming acid component and n is a number of at least 2 and preferably of from 4 to 6. Oligomeric biguanides such as these and their production are described in British patent 702,268, in British patent 1,152,243 and in British Patent no. 1 434 040. Examples of salts of these biguanides which are suitable for incorporation in the combinations according to the invention are the corresponding watersoluble mineral acid salts, for example oligohexamethylene biguanide hydrochloride.

The triple combination of the invention can also contain a compound from the known class of bisbiguanides as the microbicidal biguanide compound (component (b)). Bis-biguanides such as these have been repeatedly described in the relevant patent literature, cf. in particular U.S. Pat. Nos. 4,420,484, 2,684,924, 2,990,425, 3,468,898, 4,022,834, 4,053,636, British patent 1,344,042 and U.S. Pat. No. 4,198,392. The following are specific examples of the bisbiguanides that can be used in the practice of the present invention:
1,2-bis-($N^5$-p-chlorophenyl-$N^1$-biguanido)-ethane, 1,2-bis-($N^5$-p-nitrophenyl-$N^1$-biguanido)-ethane,chlorobenzyl-$N^1$-biguanido)-ethane, 1,2-bis-($N^5$-p-bromophenyl-$N^5$-hexyl-$N^1$-biguanido)-ethane, 1,2-bis-($N^5$-p-chlorophenyl-$N^5$-2-ethylphenyl-$N^1$-biguanido)-ethane, 1,2-bis-($N^5$-p-chlorophenyl-$N^1$-ethyl-$N^1$-biguanido)-ethane, 1,2-bis-($N^5$-p-methoxyphenyl-$N^1$-biguanido)-ethane, 1,2-bis-($N^5$-p-methylphenyl-$N^1$-biguanido)-ethane, 1,2-bis-($N^5$-3,5-dimethylphenyl-$N^1$-biguanido)-ethane, 1,2-bis($N^5$-2,6-dichlorophenyl-$N^1$-biguanido)-ethane, 1,2-bis($N^5$-2,6-dimethylphenyl-$N^1$-biguanido)-ethane, 1,4-bis($N^5$-p-chlorophenyl-$N^1$-biguanido)-butane, bis-($N^5$-p-chlorophenyl-$N^1$-biguanido)-methane and 1,3-bis-($N^5$-p-chlorophenyl-$N^1$-biguanido)-propane and water-soluble, non-toxic addition salts thereof, particularly gluconates, hydrochlorides and acetates. The particularly preferred bis-biguanide is 1,140 -hexamethylene-bis-[5(4-chlorophenyl)-biguanide] in the form of its salts, for example the acetate, hydrochloride or gluconate.

Particularly suitable microbicidal phenolic compounds (component (c) above) are o-phenylphenol (2-oxydiphenyl), benzylphenol, p-chloro-m-cresol, 2,3,4,6tetrachlorophenol, 2,4-dichlorophenol, monochlorophenylphenol, o-benzyl-p- chlorophenol, 2-cyclopentyl-4chlorophenol, chlorinated xylenols, resorcinol, thymol (3-hydroxy-p-cymol), eugenol (4-hydroxy-3-methoxy-1-allylbenzene) and carvacrol (2-hydroxy-1-methyl-4-isopropylbenzene).

In addition to the described combination of active components, the disinfectant preparations of the invention generally contain other typical components which are selected according to the particular formulation and application desired. Suitable solvents for liquid preparations are water and mixtures of water and watermiscible organic solvents, such as for example a $C_1$–$C_4$ alkanol or $C_2$–$C_6$ glycol, e.g. ethanol, isopropanol, ethylene glycol, propylene glycol, ethyl ethylene glycol and propylpropylene glycol. Solutions such as these may readily be sprayed using either compressed air or any of the propellents normally used in the aerosol field for the production of sprays. If, in addition to their antimicrobial action, the disinfectant preparations are required to show a cleaning effect, they may contain surfactants, particularly nonionic surfactants. Examples of suitable surfactants are adducts of from 4 to 40 and preferably from 4 to 20 moles of ethylene oxide with 1 mole of fatty alcohol, alkylcyclohexanol, alkylphenol, fatty acid, fatty amine, fatty acid amide or alkane sulfonamide. Of particular interest are adducts of from 5 to 16 moles of ethylene oxide with coconut oil or tallow fatty alcohols, with oleyl alcohol, with mixtures of oleyl and cetyl alcohol and with mono-, di- or trialkylphenols and monoalkylcyclohexanols containing from 6 to 14 carbon atoms in the alkyl groups. Mixed adducts of ethylene oxide and propylene oxide with the above compounds containing an active hydrogen atom are also suitable. The alkylene oxide adducts discussed above can also be closed by terminal groups, for example by ether or acetal groups.

The disinfectant preparations of the invention can also contain builders, such as for example alkali metal salts of gluconic acid, particularly sodium gluconate, alkali metal salts of nitrilotriacetic acid, ethylenediamine tetraacetic acid, hydroxyethane diphosphonic acid, phosphonobutane tricarboxylic acid, lactic citric acid or tartaric acid. Other suitable builders are the water-soluble salts of relatively high molecular weight polycarboxylic acids, for example polymers of maleic acid, itaconic acid, fumaric acid and citraconic acid. Co-polymers of these acids with one another or with other polymerizable monomers, such as for example ethylene, propylene, acrylic acid, vinylacetate, isobutylene, acrylamide and styrene, can also be used.

The disinfectant preparations of the invention can also contain cleaning boosters, such as fatty acid mono- and diethanolamides, for example coconut oil fatty acid monoethanolamide and coconut oil fatty acid diethanolamide, and adducts of up to 4 moles of ethylene oxide or propylene oxide with alkylamines containing from 12 to 18 carbon atoms or fatty alcohols containing from 8 to 12 carbon atoms and free fatty alcohols containing from 8 to 12 carbon atoms, and also cellulose-based detergency boosters.

The disinfectant preparations are normally blended with addition of dyes and perfumes. The disinfectant preparations generally have a pH value of from 4 to 10. If necessary, the pH-value is adjusted with citric acid or sodium hydroxide.

The preparations according to the invention are especially suitable for surface disinfection in hospitals, schools, public baths, public transport, and in commercial undertakings, such as hotels and laundries. The disinfection solutions intended for application are made up in such a way that they generally contain from 700 to 4500 ppm of the combination of components (a), (b) and (c), particularly when made up in spray form.

Where the solutions for application are not spray preparations, the solutions to be used are conveniently prepared from disinfectant concentrates, preferably having the following composition:

from 5 to 20 % by weight microbicidal ammonium compound
from 1 to 4 % by weight microbicidal biguanide compound,
from 0.5 to 4 % by weight microbicidal phenolic compound
and, optionally, surfactants, builders, cleaning boosters, detergency boosters and organic solvents and also ad 100% by weight water.

The invention will be illustrated but not limited by the following examples.

EXAMPLES

EXAMPLE 1

To test the microbicidal activity of a disinfectant combination in accordance with the invention, a concentrate (product A) was prepared by mixing the following individual constituents (pbw = parts by weight)

15 pbw $C_{12}$–$C_{14}$ alkylbenzyldimethylammonium chloride
(70% $C_{12}$; 30% $C_{14}$)
2 pbw oligohexamethylene biguanide hydrochloride, n=4 to 6
2 pbw o-phenylphenol
8 pbw adduct of 10 moles ethylene oxide with 1 mole nonylphenol
1 pbw sodium gluconate
0.8 pbw ethylenediamine tetraacetic acid, tetrasodium salt
1 pbw coconut oil fatty acid monoethanolamide
70.2 pbw water A product B was prepared from the same constituents, except for the deletion of the o-phenylphenol, the use of 72.2 pbw water, for comparison purposes comparison concentrate (product C) was prepared by replacing the $C_{12}$–$C_{14}$ alkylbenzyldimethylammonium chloride in the above formulation by the same quantity of didecyldimethylammonium chloride and omitting the o-phenylphenol.

The microbicidal action of 1.5% and 1% by volume dilutions of concentrates A, B and C was tested against the following test germ suspensions:

| 1) Staphylococcus aureus | $>10^8$ germs/ml |
| 2) Escherichia coli | $>10^8$ germs/ml |
| 3) Pseudomonas aeruginosa | $>10^8$ germs/ml |
| 4) Proteus mirabilis | $>10^8$ germs/ml |
| 5) Candida albicans | $>10^7$ germs/ml |

The destruction times of the test substances were determined by the germ carrier test in accordance with the Guidelines for Testing and Evaluating Chemical Disinfection Processes, 1st Part, of the Deutsche Gesellschaft fur Hygiene und Mikrobiologie, printed in Zbl. Bakt. Hyg., 1. Abt. Orig. B 172, 534–562. The destruction times determined are shown in Table 1 below.

EXAMPLE 2

A surface disinfectant concentrate was prepared by mixing the following individual constituents:
15 pbw $C_{12}$–$C_{14}$ alkylbenzyldimethylammonium chloride
(70% $C_{12}$; 30% $C_{14}$)
4 pbw oligohexamethylene biguanide hydrochloride, n=4 to 6
4 pbw o-phenylphenol 7 pbw adduct of 5 moles ethylene oxide and 4 moles propylene oxide with 1 mole $C_{12}$–$C_{14}$ fatty alcohol
1 pbw sodium gluconate
8.3 pbw nitrilotriacetic acid, trisodium salt
1 pbw phosphonobutane tricarboxylic acid
5 pbw urea
ad 100 pbw dye, perfume, water

EXAMPLE 3

A surface disinfectant concentrate was prepared by mixing the following individual constituents:

20 pbw $C_{12}$–$C_{14}$ alkylbenzyldimethylammonium chloride
(70% $C_{12}$; 30% $C_{14}$)
3 pbw oligohexamethylene biguanide hydrochloride n=4 to 6
5 pbw o-phenylphenol
10 pbw adduct of 10 moles ethylene oxide with 1 mole oleyl/cetyl alcohol mixture
1 pbw coconut oil fatty acid monoethanolamide
1 pbw ethylenediamine tetraacetic acid, tetrasodium salt
4 pbw urea
ad 100 pbw dye, perfume, water.

What is claimed is:

1. A liquid aqueous disinfectant composition comprising:
   (a) $C_{12}$–$C_{14}$ alkylbenzyldimethylammonium chloride,
   (b) oligohexamethylene biguanide hydrochloride of the formula

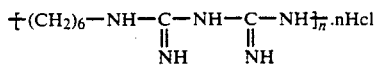

wherein n is a whole number of from 4 to 6, and
   (c) p-phenylphenol,
and wherein the ratio by weight of components (a):(b):(c) is about 15:2:2.

2. A method for disinfecting a surface comprising applying thereto a disinfecting quantity of the composition of claim 1.

* * * * *